United States Patent [19]
Dobruskin

[11] Patent Number: 4,957,493
[45] Date of Patent: * Sep. 18, 1990

[54] METHOD OF AND DEVICE FOR PRESERVING BIOLOGICAL AND MEDICAL ACTION OF SUBSTANCES BASED ON ELECTRICAL CHARGE AND/OR STATE

[76] Inventor: Moysei Dobruskin, 483 Ocean Pkwy., Brooklyn, N.Y. 11218

[*] Notice: The portion of the term of this patent subsequent to Jan. 16, 2007 has been disclaimed.

[21] Appl. No.: 340,268

[22] Filed: Apr. 19, 1989

Related U.S. Application Data

[63] Continuation-in-part of Ser. No. 126,872, Nov. 30, 1987, Pat. No. 4,894,061.

[51] Int. Cl.⁵ .......................... A61F 2/66; A61B 19/00
[52] U.S. Cl. .................................. 604/403; 215/12.1; 215/12.2; 361/212; 604/55
[58] Field of Search ......................... 604/55, 265, 403; 215/12.1, 12.2; 361/212; 128/1 R

[56] References Cited
U.S. PATENT DOCUMENTS 4,540,403 9/1985 Theeuwes ............................. 604/85
4,822,339 4/1989 Tran .................................. 604/891.1

Primary Examiner—Allen M. Ostrager
Attorney, Agent, or Firm—Ilya Zborovsky

[57] ABSTRACT

A device and a method preserve biological and medical action of substances based on electrical charge and/or state by supplying additional energy to the substance so as to prevent decrease of electrical charge and/or state thereof.

17 Claims, 3 Drawing Sheets

METHOD OF AND DEVICE FOR PRESERVING BIOLOGICAL AND MEDICAL ACTION OF SUBSTANCES BASED ON ELECTRICAL CHARGE AND/OR STATE

CROSS REFERENCE TO RELATED APPLICATION

This application is continuation-in-part of application Ser. No. 126,872 now U.S. Pat. No. 4,894,061 filed on Nov. 30, 1987.

BACKGROUND OF THE INVENTION

The present invention relates to a method of and a device for preserving biological and medical action (activity) of substances based on electrical charge and-/or state.

It has been determined that biological and medical substances having electrical charge and/or state possess pronounced bacteriocidal, virocidal and other properties for curing respective sicknesses and preventing the latter, as well as for stimulating immune system. Such a substance can include positively charged atom ions of silver, copper, gold, platinum and other metals or their mixtures and alloys. It can include electrically excited atoms and molecules of water with the above mentioned metals. It can further includes the above water with electrically excited atoms and molecules plus certain medications. Finally, it can includes all three components, namely the above water with excited atoms and molecules, plus the positively charged ions of metals, plus respective medications.

The positively charged atom ions of metals, and the "excited" water can be produced by high energy actions, such as light of high intensity, high temperature and pressure, laser beam, electrical discharge in liquid, powerful electrical and/or magnetic fields, beams of electrically charged particles, ultrasound, or their combinations. The virocidal and other properties of the substance depend on the value of its electrical charge and excited state of liquid, as well as ions of metals and medications in it. The substance action is related to non-valent electroexchange interactions with viruses, including AIDS virus, or in other words deals with electrical transfer of charges.

The above listed substances are of tremendous importance in the present bacteriological and virological situation with wide spread of bacterial and viral diseases, especially AIDS spreading as pandemia. The substances of the above type can be used for profilaxis and curing such diseases.

The time of relaxation of water and water solutions of atom ions of metals and medications depends on the value of energy supplied to them (i.e. level of inversions), storage conditions, conditions of electroexchange on a surface of a storage container, pH and storage time. Optimal pH is 7.0-7.3. Electronic structure of the substance is also very sensitive to the action of light, heat (about 100° C.), electrostatic, magnetic and electromagnetic fields, radiation, vibrations. All these factors deactivate the substance by reducing the level of electrical charge and excited state, or completely annihilating the same.

SUMMARY OF THE INVENTION

Accordingly, it is an object of the present invention to provide a device for and a method of the above mentioned type, which avoid the disadvantages of the prior art.

In keeping with these objects and with others which will become apparent hereinafter, one feature of the present invention resides, briefly stated in a device which has a container for accommodating any of the above mentioned substances, and additional means for at least preventing decrease of electrical charge and/or state of the substance accommodated in the container.

Another feature of the present invention is to provide a method in accordance with which a container accommodating any of the substances is provided with a layer which at least prevents loses of electric charge and/or state.

When the container is designed and the method is performed in accordance with the present invention, they avoid the above explained disadvantages of the prior art.

The novel features of the present invention are set forth in particular in the appended claims. The invention itself, however, both as to its construction and its method of operation, will be best understood from the following description of preferred embodiments which is accompanied by the following drawings.

DESCRIPTION OF PREFERRED EMBODIMENTS

Figure 1:
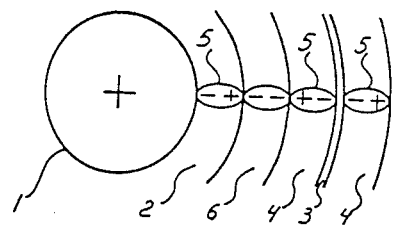
FIG. 1 is a view showing a device which accommodates the respective substance and provided with means for preventing loses of its electrical charge

FIG. 1 shows a container of inventive device for accommodating a respective substance which is identified with reference numeral 1. The wall of the container is composed of several layers. An inner layer 2 is formed of a dielectric such as for example polyethelene. This layer directly separates the substance from all other layer so as to form a phase separating structure. Molecules of the layer 2 are polarized from the outer side by the electrostatic field of a layer 6 and from the inner side by the field of the respective substance 1. The polarized molecules of dipoles 5 of the layer 2 are oriented in a certain fashion. The layer 6 is a dielectric which during its manufacture is impregnated with negative static electricity. In the shown embodiment the electrostatic energy of the layer 6 is transformed into energy of charging of the respective substance by the induction process. The layer 6 is a generator of energy. A layer 4 is an insulator and can be composed of polyester with polarized and spacially oriented molecules. A layer 3 is formed as a Faraday cage or a metal casing which screens or protects the whole container from the action of external electromagnetic fields, electrostatic charges, radiation, light, heat etc.

Figure 2:
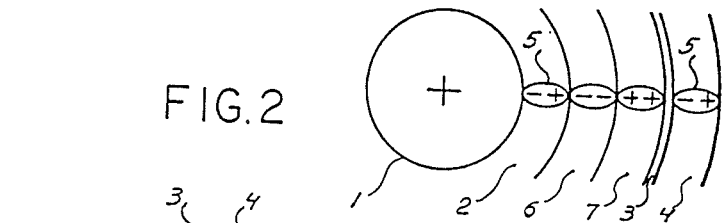
FIGS. 2-5 are views showing the device in accordance with further embodiments of the loses preventing means for the substance.

The wall of the container shown in FIG. 2 is composed of five layers. Layers 6 and 7 are energy generating layers. The layer 7 is formed from a dielectric impregnated during its manufacture with positive static electricity. In this construction the electrostatic energies of the layers 6 and 7 are added and doubled. The energy of these layers induce the respective substance. The layers 6 and 7 are thin ion-exchange membranes on the basis of high molecular compositions which possess positively or negatively charged fixed ions.

Figure 3:
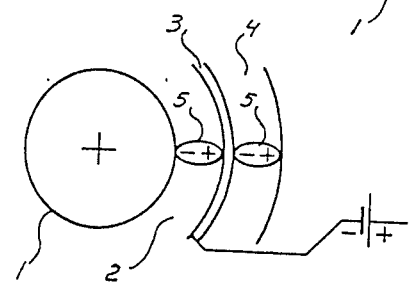

The wall of the container shown in FIG. 3 is composed of three layers. The Faraday cage here is supplied with a static energy from a battery 8. In this construction the silver cations are additionally charged by induction.

Figure 4:
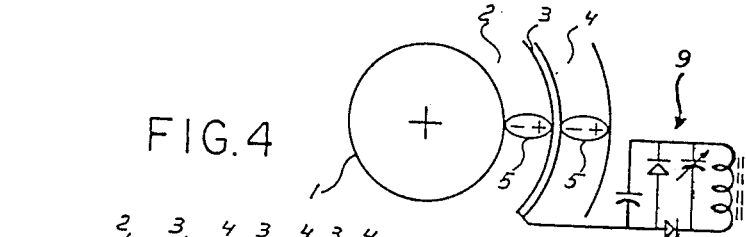

The wall of container of FIG. 4 has three layers, similarly to FIG. 3. The screen layer 3 here is supplied with energy of an external electromagnetic field from a convertor 9. The circuit of the convertor 9 is tuned to a nearby powerful radio station.

Figure 5:
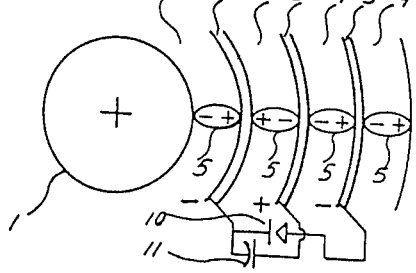

The container of FIG. 5 has seven layers. Three of these layers are formed as a Faraday cage. They form screens which not only protect the construction from the external fields, but also accumulate the energy of external fields. With the aid of a diode 10 and condensor 11 this energy is concentrated on the inner screen 3, and from there is induced into the respective substance.

The containers shown in FIGS. 6-12 can have constructions which can correspond to any of the constructions of FIGS. 1-5. However, here there are means for extra activation of the respective substance before its use.

Figure 6:
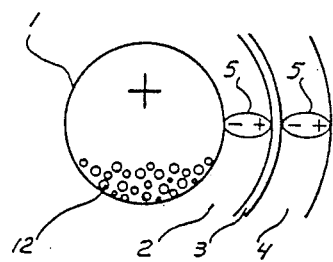
FIG. 6 is a view showing a device which accommodates the respective substance and provided with means for increasing electrical charge and/state of the same.

The container of FIG. 6 with the respective substance has small spheres from fluoroplastic, polyethelene etc. which are freely accommodated in the container. Before use, the container must be shaken. Under the action of friction, the spheres are electrified in the solution. The respective substance receives powerful additional positive charge required for superactivation.

Figure 7:
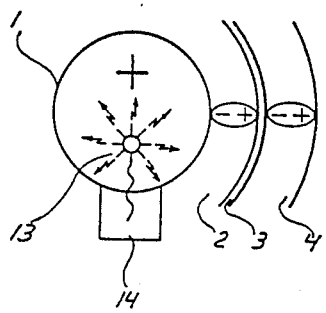
FIGS. 7-13 are views showing the device in accordance with further embodiments of the charge and/or state increasing means in accordance with the present invention.

The container in FIG. 7 has a piezo electric convertor 14 of mechanical energy into electrostatic energy, for example with potential of 5-10 kV. It is located outside of the container. Inside the container in the respective substance, there are needles for flowing off the electrical charges into the substance to provide the activation. The piezo electric convertor is actuated manually by a user.

Figure 8:
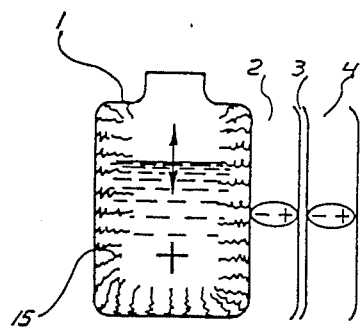

The container of FIG. 8 is provided on the inner surface of the layer 2 with a plurality of hairs and spirals composed of readily electrifyable plastic. During shaking of the container, the respective substance rubs against the hairs and spirals and is strongly electrified, to obtain additional electrical charges.

Figure 9:
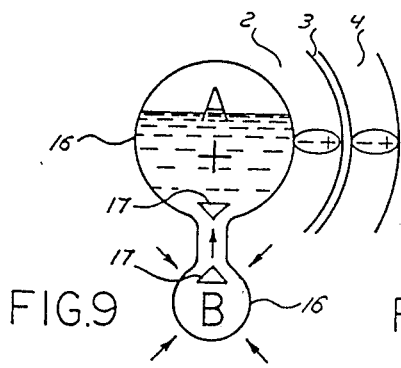
Figure 10:
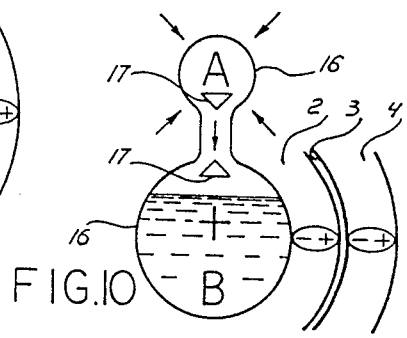
Figure 11:
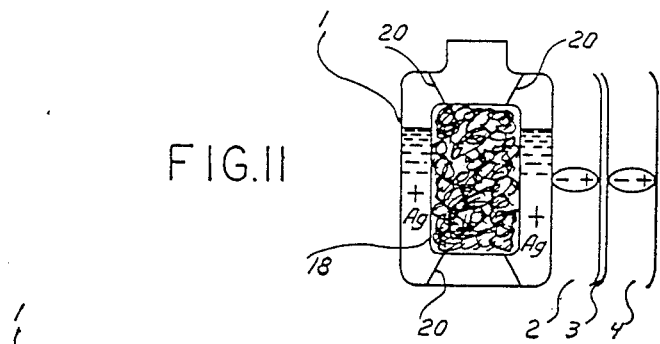
Figure 12:
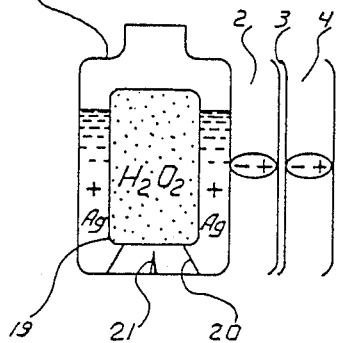
Figure 13:
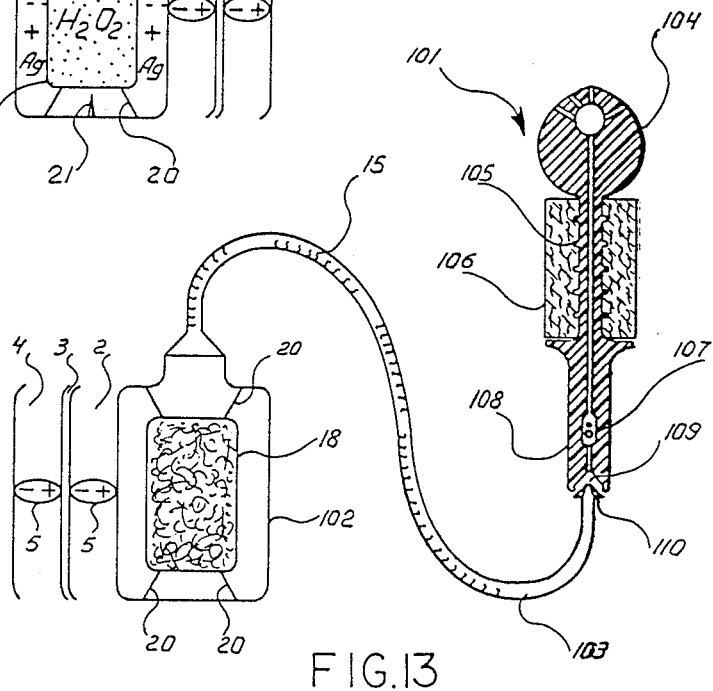

The containers of FIGS. 9 and 10 each have two spherical members A and B with elastic walls 16 with a construction similar to the constructions of FIGS. 1-5. The spherical members are connected with one another by a thin pipe with Faraday cones of readily electrifyable plastic at each end. During alternating squeezing the spherical members and thereby pumping the respective substance powerful electrifying of the solution is produced. The electrifying takes place during striking of the substance against the cones and its atomization, resulting in the activation of the solution.

The container with respective substance shown in FIG. 11 has in it a hermetically closed plastic pack with a thermogenerator. The walls of the pack and the container are elastic and interconnected as identified with reference numeral 20. When the container is squeezed, the substance is electrified from friction, and simultaneously the solution is heated by the thermogenerator which is formed as known.

In the container of FIG. 12 there is a hermetically closed pack with hydrogen peroxide 19 and a perforating needle 21. The container and the pack are interconnected at 20. During squeezing of the container the needle 21 pierces the pack 19 and the hydrogen peroxide is mixed with the respective substance. During this process free oxygen action is added to the substance and its bactericidal effect is increased.

In FIG. 13 an elastic container 102 is formed as one of the containers shown in FIGS. 1–5 It has a hermetic thermogenerator 18. The container is connected by a pipe 103 with a special attachment 101 for disinfection of a vagina. The pipe 103 is provided with hairs and spirals which are electrified during flowing of the substance therethrough under the action of friction and give their static electricity to the solution. The attachment is provided with a condensing absorbing tampon 106 which swells under the action o liquid and retains the substance in the vagina during a required time.

The attachment has a directing head nozzle 104 with a shaft 105 with a conical surface 109, with which a nozzle 110 of the pipe 103 cooperates. An inflow valve 107 is located in the handle 108. The attachment is inserted into vagine, the substance is supplied into and discharged from the head nozzle 104 through narrow passages, while the tampon swells and seals the vagina.

It should be mentioned that the wall of the container can be composed of polyethylene, fluoroplastic or tetrafluoroethylene.

It should also be mentioned that in the embodiment of FIG. 5 the Faraday cage layers 3 can perform different functions. For example, the innermost layer 3 can be composed of lead to shield the radiation, the middle layer 3 can be composed of copper to shield from external static and electromagnetic fields, and the outermost layer 3 can be composed of iron to shield from magnetic actions.

It has been found in experiments that when the substance is stored in the inventive device in accordance with the inventive method, its virocidal effect on virus AIDS increases by 12–15% as compared with a control substance which had not been stored this way.

The layers around the container can be of different thicknesses, for example between 0.1 and 1 mm.

The invention is not limited to the details shown since various modifications and structural changes are possible without departing in any way from the spirit of the invention.

What is desired to be protected by Letters Patent is set forth in the appended claims.

I claim:

1. A method of preserving biological and medical action of substances based on electrical charges and/or states, comprising the steps of accommodating a substance in a container; and supplying additional energy to the substance for preventing decreases of electrical charge and/or state of the substance.

2. A device for preserving biological and medical action of substances based on electrical charges and/or states, comprising a container with a wall bounding an inner chamber for accommodating a substance; and means for supplying additional energy to the substance so as to prevent decreases of electric charge and/or state of the substance.

3. A device as defined in claim 2, wherein said means includes a layer which contains a negative electric charge.

4. A device as defined in claim 3, wherein said means includes a layer formed as a screening Faraday cage.

5. A device as defined in claim 4; and further comprising an electrical source connected with said Faraday cage and supplying energy thereto.

6. A device as defined in claim 4; and further comprising means for converting energy of external electromagnetic field and supplying the same to said Faraday cage.

7. A device as defined in claim 4; and further comprising means for accumulating energy of external electromagnetic field in said Faraday cage.

8. A device as defined in claim 2, wherein said means includes a plurality of small bodies which are freely accommodated in the substance and electrifyable upon shaking the container.

9. A device as defined in claim 2, wherein said means includes a piezoelectric convertor arranged to convert mechanical energy applied by a user into electrostatic energy.

10. A device as defined in claim 2, wherein said means includes a plurality of small formations fixed to said wall and electrifyable during shaking of the container.

11. A device as defined in claim 2, wherein said wall forms two container portions which communicate with one another and are squeezable for pumping the substance from one container portion to the other with electrifying the substance, so as to form said means.

12. A device as defined in claim 2, wherein said means includes a thermogenerator for heating the solution.

13. A device as defined in claim 2, wherein said means includes a hydrogen peroxide pack arranged inside said wall and pierceable so as to release the hydrogen peroxide into the substance.

14. A container as defined in claim 2; and further comprising an attachment communicating with said chamber of said wall and having a nozzle head arranged to be inserted into a vagina for supplying into the latter the substance from said chamber, and a swellable tampon arranged to swell by a liquid and to seal the vagina.

15. A device as defined in claim 14; and further comprising a communicating pipe which connects said chamber with said head and is provided with means for activating the substance during its flow through said pipe from said chamber to said head.

16. A device for preserving biological and medical action of substances based on electrical charge and/or state, comprising
a container having a wall bounding an inner chamber for accommodating a substance; and
means for supplying additional energy to the substance so as to prevent decrease of electric charge and/or state of the substance accommodated in the inner chamber, said means including a layer associated with said wall and electrically charged so as to additionally charge the substance through said wall.

17. A device for preserving biological and medical action of substances based on electrical charge and/or state, comprising
a container having a wall bounding an inner chamber for accommodating a substance; and
means for supplying additional energy to the substance so as to prevent decrease of electrical charge and/or state of the substance accommodated in the inner chamber, said means including a plurality of bodies accommodated in said inner chamber and electrically chargeable so as to additionally charge the substance in said inner chamber.

* * * * *